US00PP17588P2

(12) United States Plant Patent

Kanaya

(10) Patent No.: US PP17,588 P2

(45) Date of Patent: Apr. 10, 2007

(54) *CALIBRACHOA* PLANT NAMED 'SUNBELFLAM'

(50) Latin Name: ***Calibrachoa* sp.**
Varietal Denomination: Sunbelflam

(75) Inventor: Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/259,234

(22) Filed: Oct. 26, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Calibrachoa* plant named 'Sunbelflam', characterized by its upright, outwardly spreading and mounding plant habit; vigorous growth habit; freely branching habit; freely flowering habit; long flowering period; dark pink-colored flowers with darker pink-colored centers and venation; and good weather tolerance.

1 Drawing Sheet

Botanical designation: *Calibrachoa* sp.
Cultivar denomination: 'Sunbelflam'.

BACKGROUND OF THE INVENTION

The present Invention relates to a new and distinct cultivar of *Calibrachoa* plant, botanically known as *Calibrachoa* sp., and hereinafter referred to by the cultivar name 'Sunbelflam'.

The new *Calibrachoa* is a product of a planned breeding program conducted by the Inventor in Higashiomi, Shiga, Japan. The objective of the breeding program is to create new outwardly spreading *Calibrachoas* with large and attractive flowers.

The new *Calibrachoa* originated from a cross-pollination made by the Inventor in April, 2001, of a proprietary selection of *Calibrachoa cornuta* identified as code number 9P6, not patented, as the female, or seed, parent with a proprietary selection of *Calibrachoa cornuta* identified as code number 9L2, not patented, as the male, or pollen, parent. The new *Calibrachoa* was selected as a single plant from the resulting progeny of the cross-pollination by the Inventor in a controlled environment in Higashiomi, Shiga, Japan.

Asexual reproduction of the new cultivar by terminal cuttings in a controlled environment in Higashiomi, Shiga, Japan since September, 2003, has shown that the unique features of this new *Calibrachoa* are stable and reproduced true to type in successive generations.

SUMMARY OF THE INVENTION

Plants of the cultivar Sunbelflam have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Sunbelflam'. These characteristics in combination distinguish 'Sunbelflam' as a new and distinct cultivar of *Calibrachoa:*

1. Upright, outwardly spreading and mounding plant habit.
2. Vigorous growth habit.
3. Freely branching habit.
4. Freely flowering habit.
5. Long flowering period.
6. Pink-colored flowers with darker pink-colored centers and venation.
7. Good weather tolerance; tolerant to rain and low and high temperatures.

Plants of the new *Calibrachoa* differ from plants of the female and male parent selections in flower size as plants of the new *Calibrachoa* have larger flowers than plants of the parent selections. In addition, plants of the new *Calibrachoa* and the parent selections differ in flower color as plants of the female parent selection have red purple-colored flowers and plants of the male parent selection have light purple-colored flowers.

Plants of the new *Calibrachoa* can be compared to plants of the cultivar Sunbelochipi, disclosed in U.S. Plant Pat. No. 10,355. In side-by-side comparisons conducted in Higashiomi, Shiga, Japan, plants of the new *Calibrachoa* had larger flowers with more acute petal apices than plants of the cultivar Sunbelochipi. In addition, plants of the new *Calibrachoa* and the cultivar Sunbelochipi differed in flower color as plants of the cultivar Sunbelochipi had red purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Sunbelflam' grown in a container.

The photograph at the bottom of the sheet is a close-up view of typical flowers and leaves of 'Sunbelflam'.

DETAILED BOTANICAL DESCRIPTION

In the following description, color references are made to The Royal Horticultural Society Colour Chart, 2001 Edition, except where general terms of ordinary dictionary significance are used. Plants grown in 15-cm containers for about four months were used for the aforementioned photographs and following description. Plants were grown under conditions which closely approximate commercial production conditions during the spring in Higashiomi, Shiga, Japan in a polyethylene-covered greenhouse. During the production period, day temperatures were about 23° C. and night temperatures were about 13° C. Plants were pinched one time in the spring.

Botanical classification: *Calibrachoa* sp. cultivar Sunbelflam.

Parentage:

*Female, or seed, parent.*—Proprietary selection of *Calibrachoa* sp. identified as code number 9P6, not patented.

*Male, or pollen, parent.*—Proprietary selection of *Calibrachoa* sp. identified as code number 9L2, not patented.

Propagation:

*Type cutting.*—Terminal vegetative cuttings.

*Time to initiate roots.*—About one week at 20° C. to 25° C.

*Time to produce a your rooted plant.*—About three weeks at 20° C. to 25° C.

*Root description.*—Fine, fibrous, fleshy; light brown in color.

*Rooting habit.*—Freely branching.

Plant description:

*Plant form and growth habit.*—Annual flowering plant; upright, outwardly spreading and mounding plant habit. Vigorous growth habit.

*Plant height.*—About 12.2 cm.

*Plant diameter.*—About 35 cm.

*Branching habit.*—Freely branching, about 30 lateral branches potentially develop per plant; pinching enhances lateral branch development.

*Lateral branch description.*—Length: About 11.4 cm. Diameter: About 1.8 mm. Internode length: About 1.6 cm. Texture: Pubescent. Color: 144B.

*Foliage description.*—Arrangement: Alternate; simple. Length: About 3.9 cm. Width: About 1.4 cm. Shape: Narrowly elliptic. Apex: Obtuse. Base: Cuneate. Margin: Entire. Texture, upper and lower surfaces: Pubescent. Venation pattern: Pinnate; reticulate. Color: Developing foliage, upper surface: 143A. Developing foliage, lower surface: 147B. Fully expanded foliage, upper surface: 147A. Fully expanded foliage, lower surface: 147B. Petiole length: About 1.5 mm. Petiole diameter: About 0.3 mm. Petiole texture, upper and lower surfaces: Pubescent. Petiole color, upper and lower surfaces: 144C.

Flower description:

*Flower type and habit.*—Flowers face upright or outward; single, axillary; salverform. Flowers not persistent. Freely flowering habit, numerous flowers per plant, about two flowers develop per lateral branch. Flowers not fragrant.

*Natural flowering season.*—Spring to late autumn in Japan; flowering continuous during this period.

*Time to flower.*—Early flowering; plants begin flowering about three to four weeks after planting.

*Flower longevity on the plant.*—About seven to ten days.

*Flower size.*—Diameter: About 3.8 cm. Depth: About 3 cm. Throat diameter (distal): About 8.2 mm. Tube diameter (proximal): About 2.1 mm.

*Flower buds.*—Length: About 2.3 cm. Diameter: About 4.9 mm. Shape: Elongated oblong. Color: 72B.

*Corolla.*—Arrangement/appearance: Single whorl of five petals fused into flared trumpet. Petal length from throat: About 1.4 cm. Petal width: About 1.7 cm. Petal shape: Spatulate. Petal apex: Rounded. Petal margin: Entire. Petal texture, upper and lower surfaces: Smooth, glabrous; satiny. Color: Petal, when opening, upper surface: N74B; towards the throat, N74A. Petal, when opening, lower surface: 75A; venation, N77A. Petal, fully opened, upper surface: N74C; towards the throat, N74B. Petal, when opening, lower surface: 77C. Flower throat (inside): 13A; venation, N77A or 148A. Flower tube (outside): 154D; venation, N77A.

*Sepals.*—Arrangement/appearance: Single whorl of five sepals fused at base; star-shaped calyx. Length: About 1.6 cm. Width: About 3.4 mm. Shape: Lanceolate. Apex: Acute. Margin: Entire. Texture, upper and lower surfaces: Pubescent. Color, upper surface: 137A. Color, lower surface: 137C.

*Peduncles.*—Length: About 1.7 cm. Width: About 0.6 mm. Strength: Moderately strong. Texture: Pubescent. Color: 144A.

*Reproductive organs.*—Stamens: Quantity: Five per flower. Anther shape: Ellipsoidal. Anther length: About 1.1 mm. Anther color: 15D. Pollen amount: Moderate. Pollen color: 10D. Pistils: Quantity: One per flower. Pistil length: About 8.5 mm. Stigma shape: Ellipsoidal. Stigma color: 144B. Style length: About 5.6 mm. Style color: 144C. Ovary color: 144B.

*Seeds.*—Seed development has not been observed.

Disease/pest resistance: Plants of the new *Calibrachoa* have not been noted to be resistant to pathogens and pests common to *Calibrachoas.*

Weather/temperature tolerance: Plants of the new *Calibrachoa* are tolerant to rain and wind and have been observed to tolerate temperatures from 0° C. to 35° C.

It is claimed:

1. A new and distinct cultivar of *Calibrachoa* plant named 'Sunbelflam', as illustrated and described.

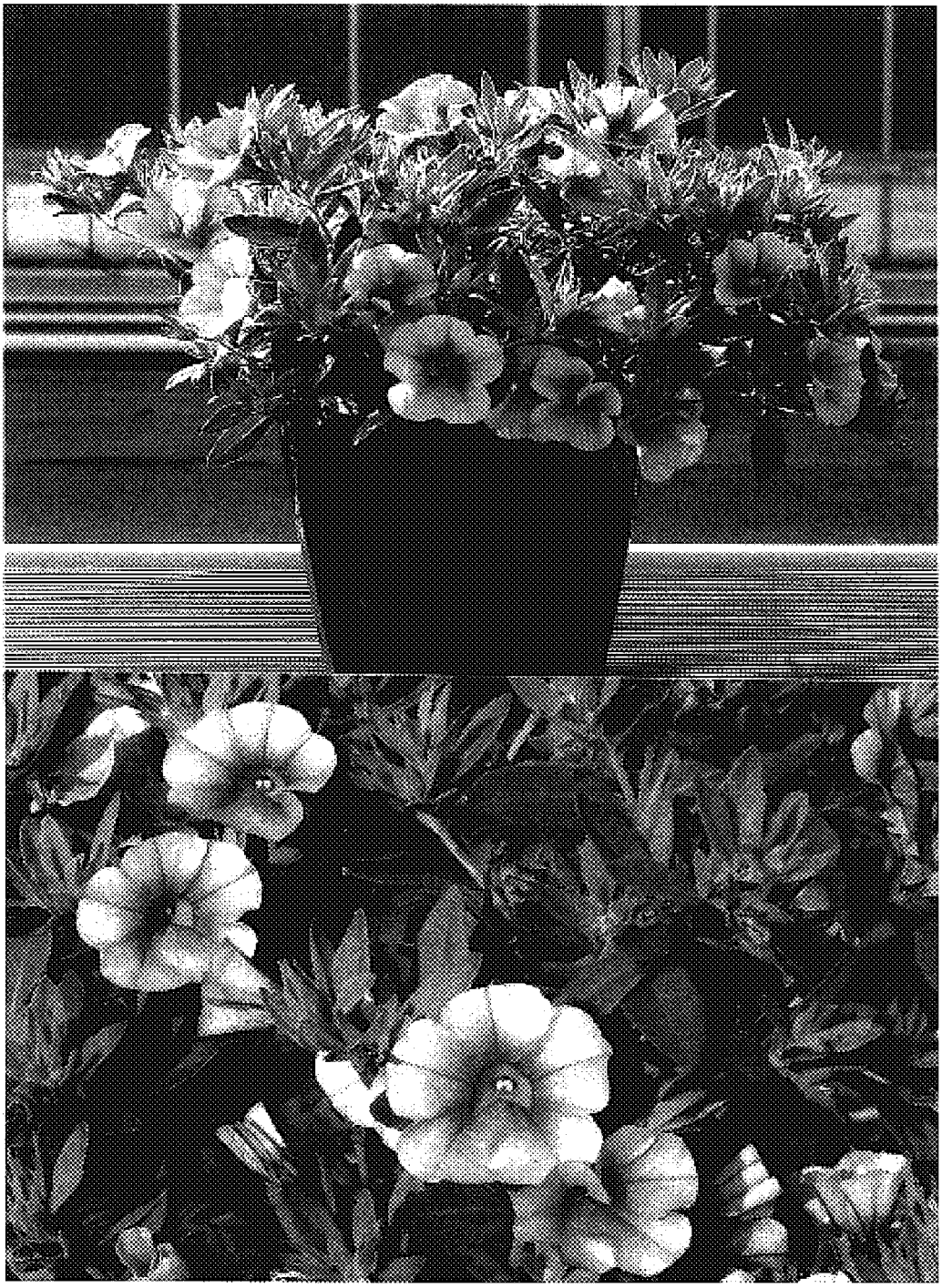

* * * * *